(12) United States Patent
Wang et al.

(10) Patent No.: US 12,186,487 B2
(45) Date of Patent: Jan. 7, 2025

(54) APPARATUS AND METHOD TO ASSESS AIRWAY CLEARANCE THERAPY EFFICACY

(71) Applicant: Hill-Rom Services PTE. LTD., Singapore (SG)

(72) Inventors: Yue Wang, Columbus, IN (US); Chau C. Ye, Singapore (SG)

(73) Assignee: Hill-Rom Services PTE. LTD., Singapore (SG)

( * ) Notice: Subject to any disclaimer, the term of this patent is extended or adjusted under 35 U.S.C. 154(b) by 0 days.

(21) Appl. No.: 17/847,423

(22) Filed: Jun. 23, 2022

(65) Prior Publication Data

US 2022/0313939 A1   Oct. 6, 2022

Related U.S. Application Data

(63) Continuation of application No. 16/456,358, filed on Jun. 28, 2019, now Pat. No. 11,395,899.

(60) Provisional application No. 62/694,115, filed on Jul. 5, 2018.

(51) Int. Cl.
| | |
|---|---|
| A61M 16/00 | (2006.01) |
| A61B 5/085 | (2006.01) |
| A61M 16/08 | (2006.01) |
| A61M 16/10 | (2006.01) |
| A61B 5/08 | (2006.01) |

(52) U.S. Cl.
CPC ........... *A61M 16/105* (2013.01); *A61B 5/085* (2013.01); *A61M 16/0003* (2014.02); *A61M 16/0858* (2014.02); *A61B 5/082* (2013.01); *A61M 2016/0027* (2013.01); *A61M 16/024* (2017.08); *A61M 2205/75* (2013.01)

(58) Field of Classification Search
CPC ............ A61M 16/105; A61M 16/0003; A61M 2016/0027; A61B 5/085; A61B 5/082
See application file for complete search history.

(56) References Cited

U.S. PATENT DOCUMENTS

| | | |
|---|---|---|
| 3,527,205 A | 9/1970 | Jones |
| 4,425,805 A | 1/1984 | Ogura et al. |
| 4,440,177 A | 4/1984 | Anderson et al. |
| 4,648,396 A | 3/1987 | Raemer |

(Continued)

FOREIGN PATENT DOCUMENTS

| | | | | |
|---|---|---|---|---|
| CA | 3066632 A1 | * | 12/2018 | ........... A61B 5/0205 |
| CN | 104473647 A | * | 4/2015 | ........... A61B 5/0004 |

(Continued)

OTHER PUBLICATIONS

Japanese Office Action for Application No. 2019-125184, dated Nov. 24, 2020, 4 pages.

(Continued)

*Primary Examiner* — Michael R Reid
*Assistant Examiner* — Sarah B Lederer
(74) *Attorney, Agent, or Firm* — Barnes & Thornburg LLP

(57) ABSTRACT

A method of assessing airway clearance therapy efficacy includes generating a pressure pulse in a respiratory device being used by a patient. The patient's lung impedance is measured during the pressure pulse and the patient's lung condition is assessed based on the patient's lung impedance. The patient's lung condition is then assessed after airway clearance therapy.

17 Claims, 14 Drawing Sheets

(56) References Cited

U.S. PATENT DOCUMENTS

| | | | |
|---|---|---|---|
| 4,796,639 A | 1/1989 | Snow et al. | |
| 4,955,946 A | 9/1990 | Mount et al. | |
| 5,060,655 A | 10/1991 | Rudolph | |
| 5,095,900 A | 3/1992 | Fertig et al. | |
| 5,179,958 A | 1/1993 | Mault | |
| 5,309,921 A | 5/1994 | Kisner et al. | |
| 5,357,972 A | 10/1994 | Norlien | |
| 5,800,360 A | 9/1998 | Kisner et al. | |
| 6,308,706 B1 | 10/2001 | Lammers et al. | |
| 6,585,662 B1 | 7/2003 | Jones et al. | |
| 6,616,615 B2 | 9/2003 | Mault | |
| 7,654,998 B1 * | 2/2010 | Ingenito | A61B 17/12136 604/514 |
| 8,460,223 B2 * | 6/2013 | Huster | A61H 9/005 601/149 |
| 2010/0228143 A1 * | 9/2010 | Teschner | A61B 5/0536 600/547 |
| 2015/0290418 A1 * | 10/2015 | Kaczka | A61M 16/18 128/200.14 |
| 2015/0320338 A1 * | 11/2015 | Kane | A61B 5/4818 600/533 |
| 2016/0045161 A1 * | 2/2016 | Alshaer | A61B 5/097 600/538 |

FOREIGN PATENT DOCUMENTS

| | | | | |
|---|---|---|---|---|
| JP | 2003070904 A | 3/2003 | | |
| JP | 2004520896 A | 7/2004 | | |
| WO | 9732619 A1 | 9/1997 | | |
| WO | 02056768 A1 | 7/2002 | | |
| WO | WO-2009113500 A1 * | 9/2009 | | A61B 5/085 |
| WO | WO-2014097047 A1 * | 6/2014 | | A61B 5/0826 |
| WO | WO-2015061848 A1 * | 5/2015 | | A61M 16/0051 |
| WO | WO-2018072036 A1 * | 4/2018 | | A61B 5/085 |

OTHER PUBLICATIONS

Extended European Search Report for Application No. 19183712.9, dated Aug. 28, 2019, 10 pages.

H. Normand et al., "Clinical evaluation of a screen pneumotachograph as an in-line filter," European Respiratory Journal, vol. 30(2): 358-363, Aug. 1, 2007, https://erj.ersjournals.com/content/30/2/358 6 pages.

Juliana Veiga Cavalcanti et al. "Using the forced oscillation technique to evaluate bronchodilator response in healthy volunteers and in asthma patients presenting a verified positive response," J. bras. pneumol, vol. 32(2): 91-8, Mar./Apr. 2006, http://www.scielo.br/scielo.php?pid=s1806-37132006000200003&script=sci_arttext&tlng=en, 8 pages.

Makito Yaegashi et al., "The utility of the forced oscillation technique in assessing bronchodilator responsiveness in patients with asthma," Respiratory Medicine, vol. 101(5), 995-1000, May 2007, http://www.sciencedirect.com/science/article/pii/S0954611106004434, 6 pages.

Christophe Delacourt et al. "Use of the Forced Oscillation Technique to Assess Airway Obstruction and Reversibility in Children," American Journal of Respiratory and Critical Care Medicine, vol. 161(3), 730-736, Mar. 1, 2000, http://www.atsjournals.org/doi/full/10.1164/ajrccm.161.3.9904081, 7 pages.

Cheol Woo Kim, M.D. et al., "Clinical Applications of Forced Oscillation Techniques (FOT) in Patients with Bronchial Asthma," The Korean Journal Of Internal Medicine, vol. 16(2): 80-86, Jun. 2001, https://www.ncbi.nlm.nih.gov/pmc/articles/PMC4531717/, 7 pages.

CareFusion Respiratory Care, MasterScreen IOS, Oscillometric Impedance Measurement from JAEGER, 6 pages.

Chinese Notice of Refusal for Application No. 201910606602.4, dated Nov. 14, 2022, 5 pages. (English Translation Attached).

* cited by examiner

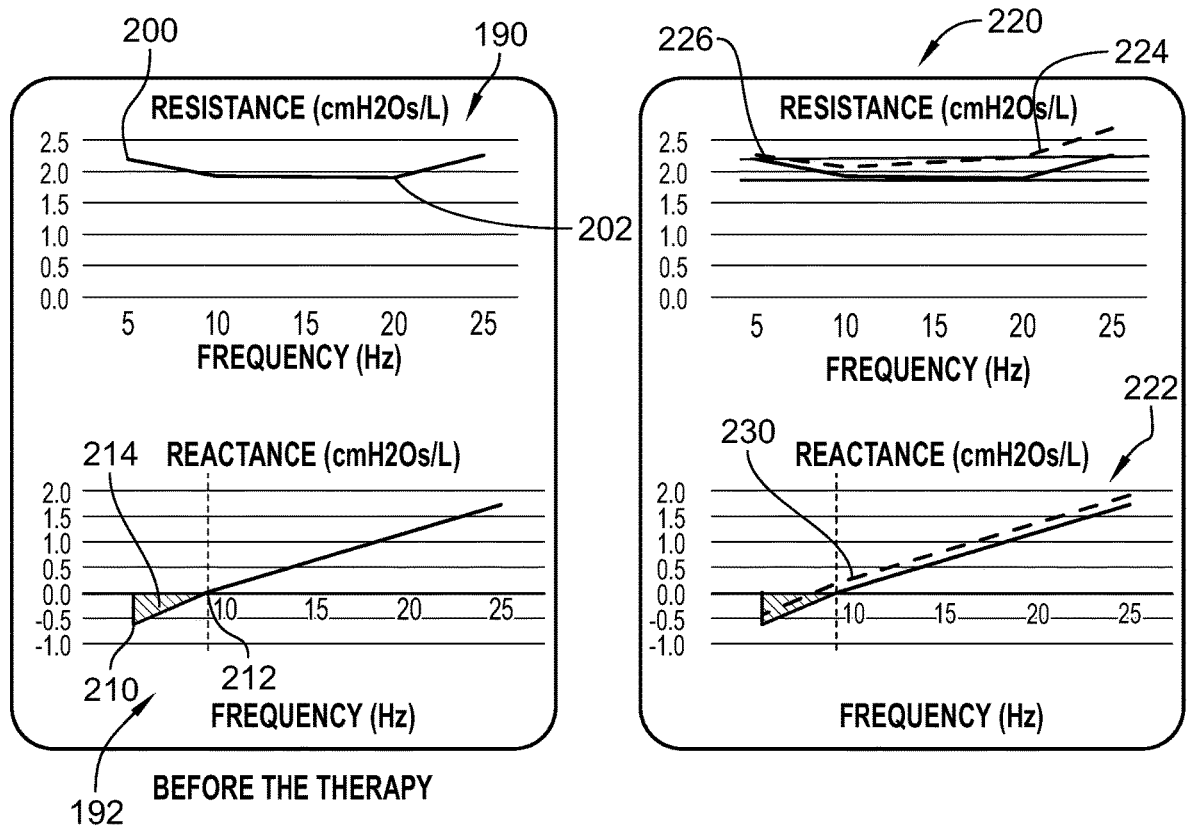
FIG. 12 BEFORE THE THERAPY
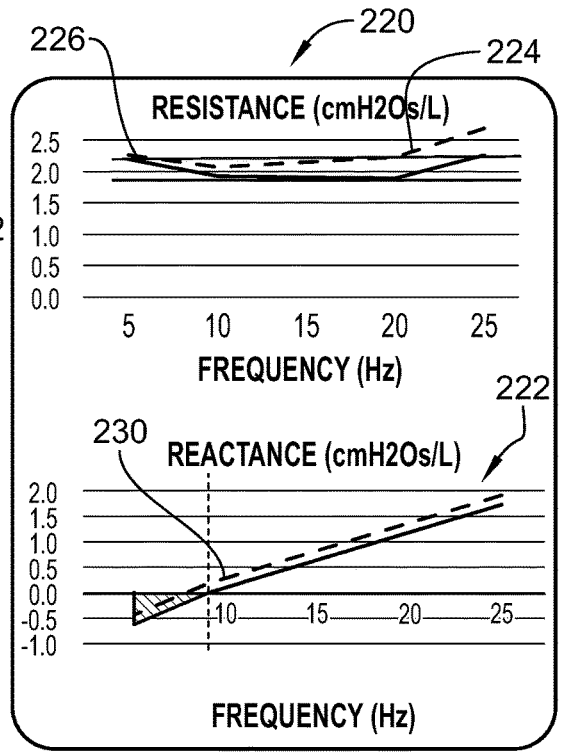
FIG. 13
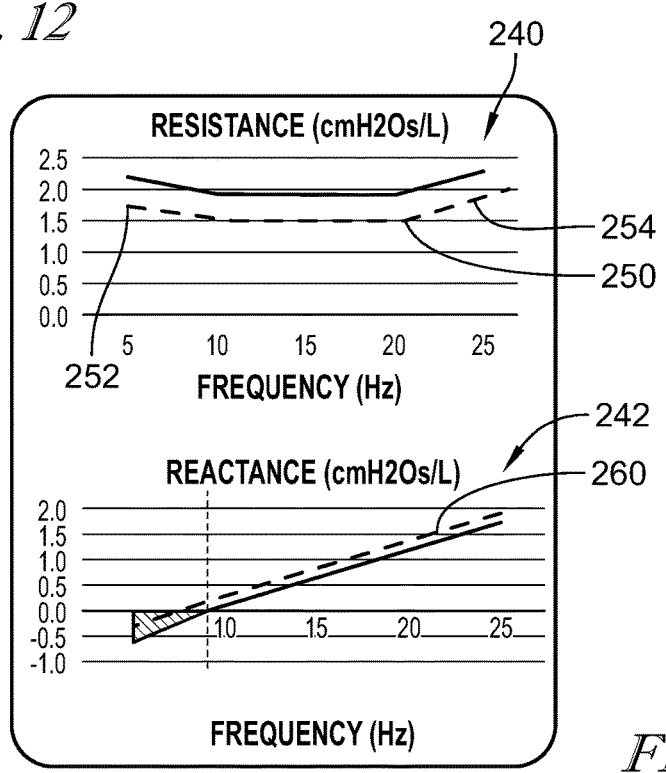
FIG. 14

APPARATUS AND METHOD TO ASSESS AIRWAY CLEARANCE THERAPY EFFICACY

CROSS-REFERENCE TO RELATED APPLICATIONS

This application is a continuation application of U.S. patent application Ser. No. 16/456,358, filed Jun. 28, 2019 and now U.S. Pat. No. 11,395,899, which claims priority under 35 U.S.C. § 119 (e) to U.S. Provisional Patent Application Ser. No. 62/694,115, filed Jul. 5, 2018, which is expressly incorporated by reference herein.

BACKGROUND

The present disclosure relates to respiratory devices. More particularly, the present disclosure relates to a respiratory device and method for assessing airway clearance therapy efficacy.

There is no good objective/standard method to assess airway clearance therapy efficacy at home for both clinicians and patients. The need to rationalize the utilization of health care resources together with the optimization of patient's care has prompted the development of models of assistance based on home monitoring. At the present time, most of the suggested models are based on the utilization of diaries for symptoms perceived by the patients. Even if positive results are reported in terms of reductions in hospitalization, many patients tend to underestimate the severity of their condition and their compliance in recording their symptoms rapidly decreases with time. There is no frequent/close monitoring for patients who receive airway clearance therapy at home. Attempts of using more objective measurements such as home spirometers have been done but poor results have been reported mainly due to the difficulties in performing a spirometric test without medical supervision.

More often than not, patients do spirometry in clinics every 3-6 months during follow-up sessions. During gaps, there is no way for clinicians to track the patient's lung condition and the patient's interaction with airway clearance therapy. Even for a spirometric test done in a lab, spirometry appears to be a very effort-dependent test and sometimes clinicians do not even trust its results. Spirometry is not suitable for certain populations such as young kids, the elderly, and patients with Neural muscular disease (NMD). In such scenarios, clinicians have to rely on the patients' self-declaration about their conditions.

One technique in assessing airway clearance therapy efficacy is based on measuring the impedance of the patient's lung through sensing of the flow and pressure drop while sending pressure pulses into the patient's lung and evaluating a modulation effect by the lung. In this measurement, there are lots of potential events that could lead to contamination of the flow rate/pressure drop signal, which could destroy the accurate interpretation of lung impedance. Those potential events are mainly unexpected artifacts such as leakage, blockage, coughing, burping, swallowing, hemming, etc. These events will either artificially increase or decrease the impedance readings and need to be identified in the signal and rejected.

SUMMARY

The present disclosure includes one or more of the features recited in the appended claims and/or the following features which, alone or in any combination, may comprise patentable subject matter.

In one aspect of the disclosed embodiments, a respiratory device may include an inlet port and an outlet port. A fluid pathway may extend between the inlet port and the outlet port. A filter housing may be positioned between the inlet port and the outlet port. A filter may be positioned within the filter housing. A first pressure port may be positioned on an inlet side of the filter housing. A second pressure port may be positioned on an outlet side of the filter housing. The first pressure port and the second pressure port may extend parallel to the fluid pathway. A pressure transducer may be coupled to the first pressure port and the second pressure port and configured to measure a pressure drop between the first pressure port and the second pressure port.

It may be desired that the filter is positioned between the first pressure port and the second pressure port. The filter may include a screen. A gasket may extend around the filter. The gasket may seal an inlet side and an outlet side of the filter. The gasket may prevent airflow around the filter.

It may be contemplated that the inlet port is coupled to a respirator. The filter housing may include an inlet segment including the inlet port and an outlet segment including the outlet port. The inlet segment and the outlet segment may be coupled together. A clamp may be provided to couple the inlet segment to the outlet segment. The clamp may seal the inlet segment to the outlet segment.

In another aspect of the disclosed embodiments, a method of assessing airway clearance therapy efficacy may include generating a pressure pulse in a respiratory device being used by a patient. The method may also include measuring the patient's lung impedance during the pressure pulse. The method may also include assessing the patient's lung condition based on the patient's lung impedance. The method may also include delivering airway clearance therapy to the patient. The method may also include assessing the patient's lung condition after the airway clearance therapy. The method may also include comparing the patient's lung impedance to the patient's lung condition after the airway clearance therapy to determine a therapy efficacy.

In some embodiments, the method may also include deriving the patient's lung resistance and lung compliance from the patient's lung impedance. The method may also include assessing the patient's lung condition based on the patient's lung resistance and lung compliance. The patient's lung compliance may be a factor of the patient's lung inertia. The method may also include deriving an overall resistance of a patient's respiratory system based on a graph of the patient's lung resistance. The method may also include deriving a resistance of a patient's conducting airways based on a graph of the patient's lung resistance.

Alternatively or in addition to, the method may also include deriving a patient's lung reactance from the patient's lung impedance. The method may also include determining a compliance of the patient's lung based on the patient's lung reactance.

Optionally, the method may also include comparing the patient's lung impedance to the patient's lung condition after the airway clearance therapy to determine a therapy efficacy further comprises comparing the patient's lung impedance before the airway clearance therapy to the patient's lung impedance after the airway clearance therapy.

In some embodiments, the method may also include detecting a deviation in a baseline of a breathing signal. The method may also include finding a new baseline for the breathing signal. The method may also include updating the baseline for the breathing signal to the new baseline. The deviation may be greater than 13 percent. The method may also include rejecting detected artifacts with a continuous presence of less than two data points. The method may also include mapping a breathing waveform onto a real time impedance curve to identify intact breathing cycles. The method may also include connecting the intact breathing cycles to calculate the patient's lung impedance.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which:

FIG. 12 illustrates graphs of a patient's lung resistance and lung reactance prior to therapy;
FIG. 13 illustrates graphs of a patient's lung resistance and lung reactance during therapy;
FIG. 14 illustrates graphs of a patient's lung resistance and lung reactance after therapy.

DETAILED DESCRIPTION

According to the disclosed embodiments, by sending a pressure pulse that contains multiple frequencies into the patients' lung, pressure and flow signals are collected, which represent the pressure drop across patient's respiratory system as well as the flow rate into and out from the patients' lung. The pressure pulse signal contains 5-25 Hz, which does not overlap with the patient's breathing frequency and is easily separated out using a Fast Fourier Transform (FFT). In addition, a 5-25 Hz pressure signal is spread out from the patient's upper airway down to the lower airway. By analyzing the pressure and flow relationship, the patient's lung impedance is derived, which includes both resistance and reactance information. This technique to derive the patient's airway impedance condition is employed to objectively assess an airway clearance device's therapy efficacy by analyzing an impedance curve change after stage 1 therapy (mucus is mobilized from lower airway to upper airway) and stage 2 therapy (mucus is facilitated to cough out). Data is sent to a remote computer for both patients and caregivers to assess. Based on the therapy efficacy assessment, clinicians decide whether a change in the therapy setting is needed or desired.

The disclosed embodiments also provide a three layer checking mechanism in the detection algorithm. In the first layer, deviation of the signal from the baseline is used as the main criteria to identify potential artifacts. The baseline is updated once a new baseline is found. In the second layer, the detected artifacts with continuous presence of less than two data points will be rejected as a false detection. In the third level, a breathing waveform is mapped onto the real time impedance curve to identify the intact breathing cycles. Breathing cycles contaminated by one or more artifacts will be rejected. The intact breathing cycles are connected to calculate the impedance, and a counter is set up to count the number of clean breathing cycles through detection of inhalation and exhalation based on detection of a slope change in the flow rate and pressure waveform. In some embodiments, a minimum number of breathing cycles of 8 may be used to ensure quality of the data.

The artifact detection/rejection mechanism is used to achieve accurate impedance measurement. Without this mechanism, the impedance measurement of the patient's lung will be contaminated by the artifacts and, therefore, lead to inaccurate results. If enough clean breathing cycles (flow rate, pressure) remain after the contaminated breathing cycles are rejected, accurate results are achieved.

Figure 1:
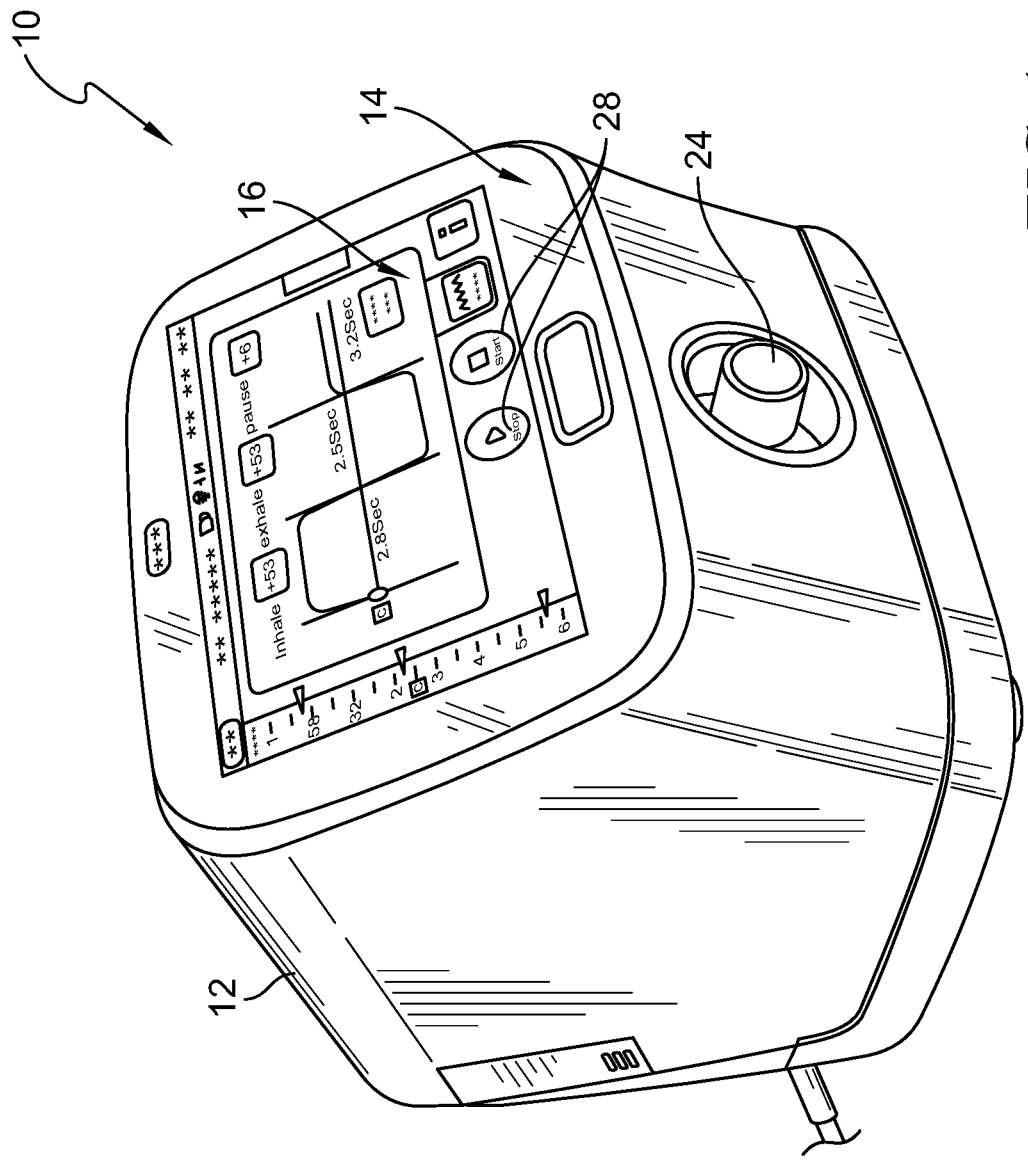
FIG. 1 is a front perspective view of a respiratory device.

A respiratory device 10 is provided in FIG. 1. The details of the structure of a suitable respiratory device and related electrical components may be found in International Application No. PCT/SG2016/050166, filed Apr. 1, 2016, published as WO 2016/159889 A1 on Oct. 6, 2016, and titled "Manifold for Respiratory Device," which is hereby incorporated herein in its entirety. See also U.S. patent application Ser. No. 15/901,114, filed Feb. 21, 2018, which is hereby incorporated herein in its entirety. Respiratory device 10 includes a housing 12 having a front wall 14 on which a display or graphical user interface 16 is accessible to enter user inputs into device 10 and to view displayed information regarding the operation of device 10 as shown in FIG. 1. At a bottom region of front wall 14 of housing 12, a hose is attached to a flow element 24. Beneath the graphical user interface 16 there is an on/off button 28 that is pressed sequentially to turn device 10 on and off.

Device 10 is operable as an insufflation/exsufflation device or, as such devices are sometimes called, a cough assist device. Thus, device 10 is capable of applying positive pressure and negative pressure to a patient's airway, the positive pressure being applied during insufflation and the negative pressure being applied during exsufflation. The device 10 may be controlled to apply the positive insufflation pressure or the negative insufflation pressure to the patient through a patient interface (not shown) that is coupled to the flow element 24. The user may select to switch between insufflation, exsufflation, and pause pressures in a manual mode of the device 10 or this is done automatically by device 10 in an automatic mode. In some embodiments, device 10 is operable to provide other modes of respiratory therapy such as continuous positive expiratory pressure (CPEP) and continuous high frequency oscillation (CHFO), just to name a couple. CPEP and CHFO are sometimes referred to herein, collectively, as Intrapulmonary Percussive Ventilation (IPV).

Figure 2:
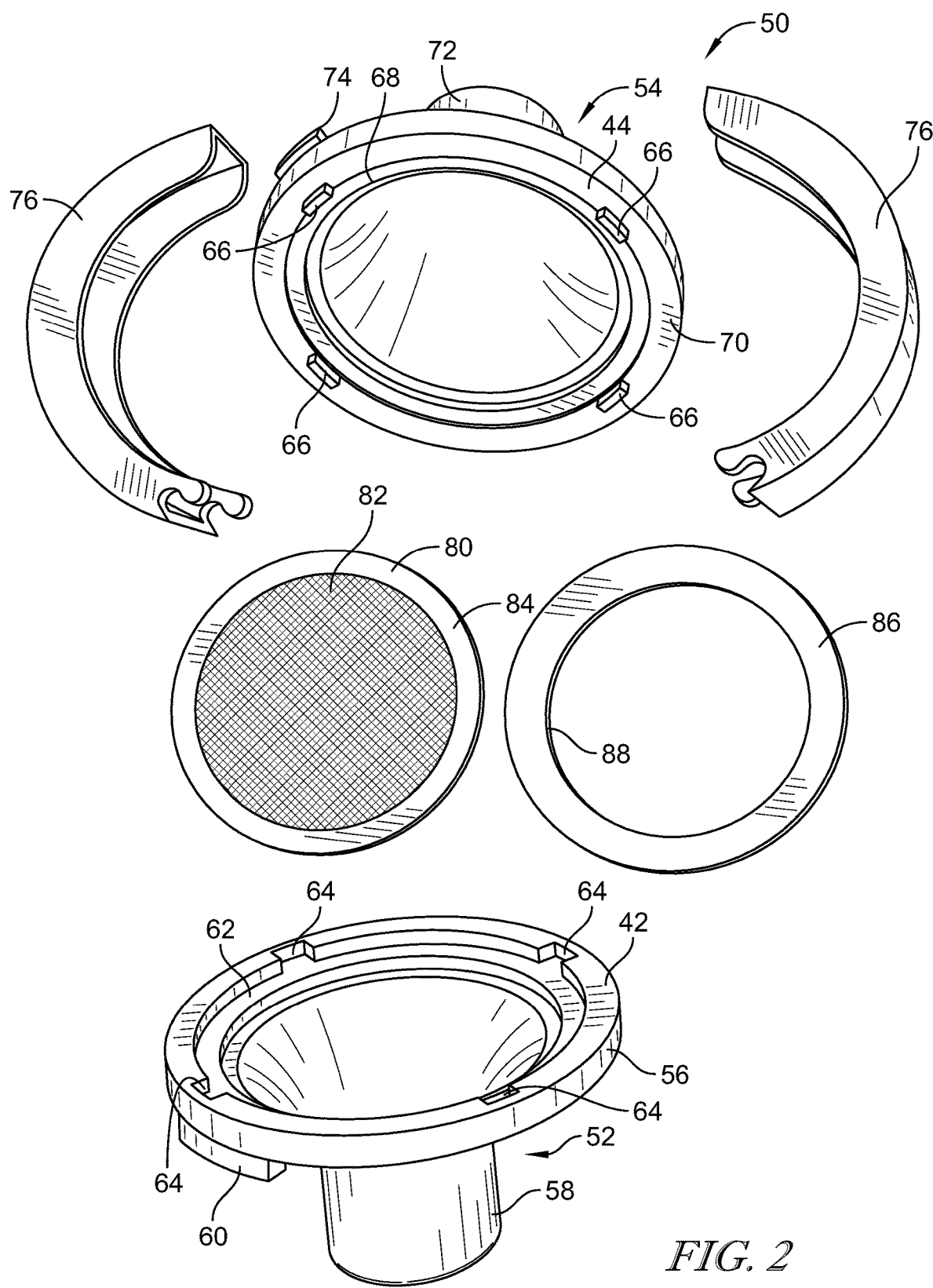
FIG. 2 is an exploded view of a flow element.

Referring to FIG. 2, the flow element 24 includes an inlet segment 52 that is configured to couple to an outlet segment 54. The inlet segment 52 includes a rounded body 56 and an inlet port 58 extending from the rounded body 56. The rounded body 56 includes a retaining flange 60 that is configured to facilitate coupling the inlet segment 52 to the outlet segment 54, as described below. A flange 42 extends around the rounded body 56. The flange 42 steps down to an inner surface 62. A plurality of notches 64 extend from the inner surface 62 into the flange 42.

The outlet segment 54 includes a rounded body 70 and an outlet port 72 extending from the rounded body 70. The outlet port 72 is configured to be coupled to a patient interface via a hose. The rounded body 70 includes an annular retaining flange 74 that is configured to facilitate coupling the inlet segment 52 to the outlet segment 54. A pair of clamps 76 is configured to engage the retaining flanges 60, 74 to secure the inlet segment 52 to the outlet segment 54. A flange 44 extends around the rounded body 70 and steps down to an inner surface 68. A plurality of tabs 66 extend from the flange 44. When the outlet segment 54 is coupled to the inlet segment 52, the flanges 42 and 44 are abutted against one another. The tabs 66 are secured within the notches 66 to align the inlet segment 52 and the outlet segment 54. The inner surfaces 62 and 68 define a cavity within the flow element 24.

Figure 3:
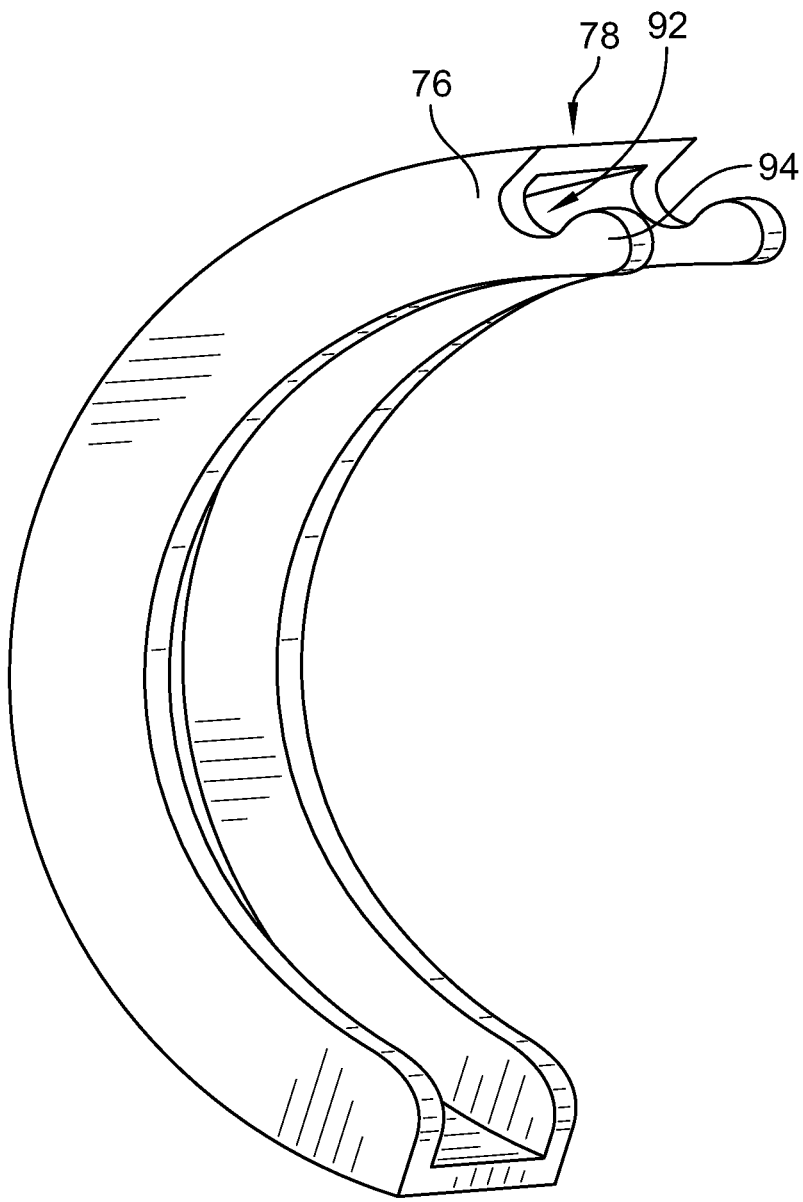
FIG. 3 is a side perspective view of a clamp.
Figure 5:
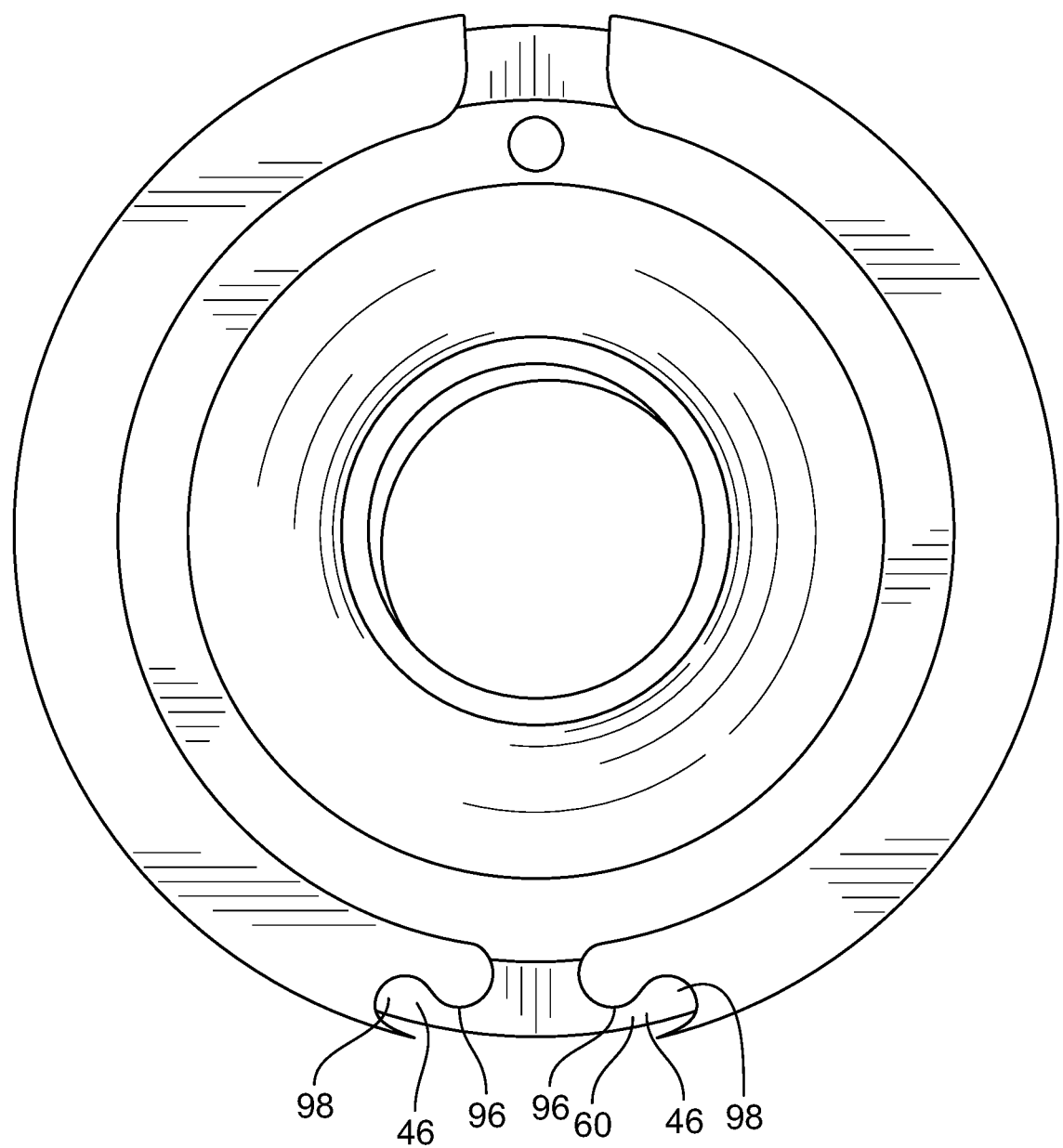
FIG. 5 is a top perspective view of the flow element.

Referring to FIG. 3, the clamps 76 include a tongue and groove configuration to couple the outlet segment 54 to the inlet segment 52. An end 78 of each clamp includes a groove 92 and a tongue 94 extending outward from the groove 92. Likewise, as shown in FIG. 5, the flange 60 also includes a tongue and groove configuration. Each end 46 includes a groove 96 and a tongue 98 extending from the groove 96. The tongues 94 of each clamp 76 are configured to secured within the groove 96 of the flange 60. Also, the tongues 98 of the flange 60 are configured to lock within the groove 92 of each clamp 76.

Figure 4:
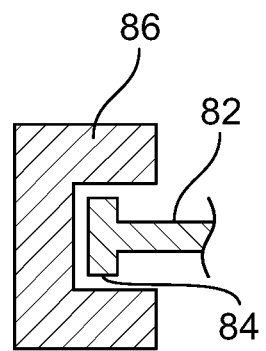
FIG. 4 is a cross-sectional view of a filter and an gasket.

A filter 80 is configured to position between the inlet segment 52 and the outlet segment 54. The filter 80 positions between the rounded body 56 of the inlet segment 52 and the rounded body 70 of the outlet segment 54 when the inlet segment 52 is coupled to the outlet segment 54. The filter 80 is retained in the cavity defined by the inner surfaces 62 and 68. In some embodiments, the filter 80 includes a screen 82 surrounded by an outer rim 84. The screen 82 and the outer rim 84 may be formed from metal or plastic. In some embodiments, the screen 82 may be a paper filter. A gasket 86 includes a groove 88 that is configured to receive the outer rim 84 of the filter 80. The gasket 86 seals the filter within the flow element 24 so that any air passing through the flow element 24 passes through the screen 82. Referring to FIG. 4, the gasket 86 seals around the outer rim 84 and a portion of the screen 82 to seal the flow element 24. Flow element 24 is sometimes referred to as a pneumotachometer or a pneumotach, for short.

Figure 6:
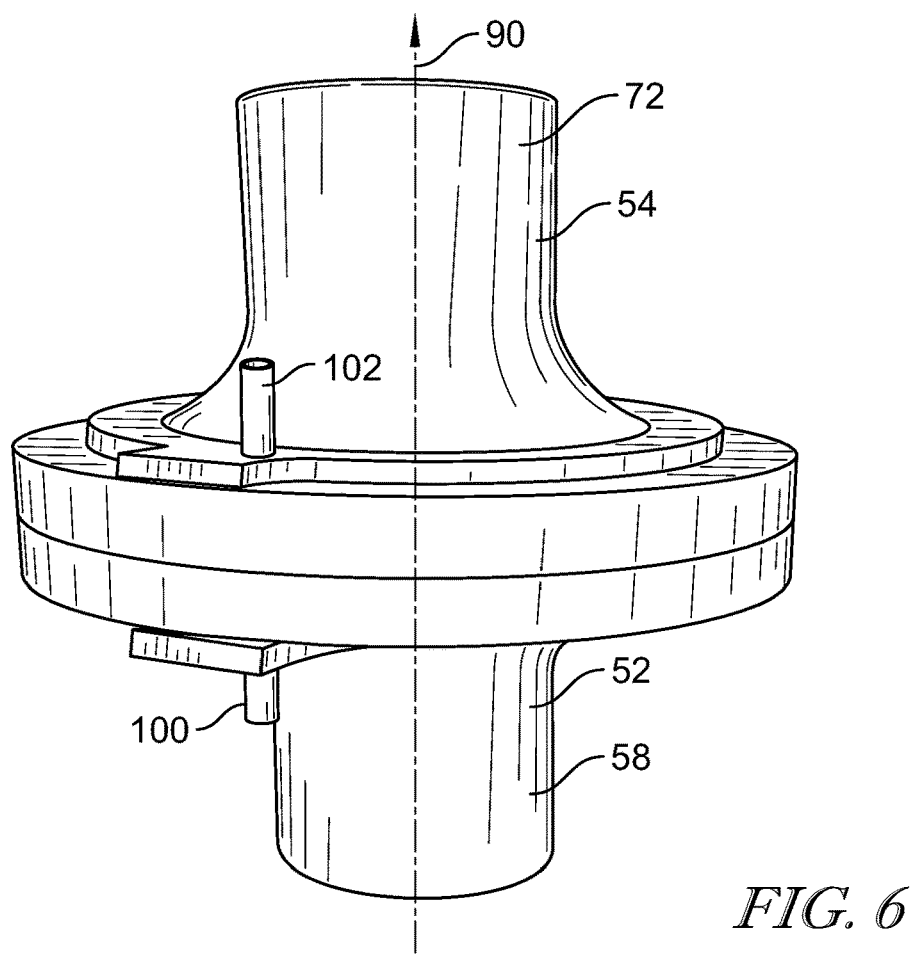
FIG. 6 is a side perspective view of the flow element shown in FIG. 1.

Referring to FIG. 6, when the inlet segment 52 is coupled to the outlet segment 54, the inlet port 58 and the outlet port 72 form a flowpath 90 through the flow element 24. In some embodiments, the flowpath 90 is a linear flowpath between the inlet port 58 and the outlet port 72. The flowpath 90 passes through the filter 80.

An inlet pressure port 100 extends from the rounded body 56 of the inlet segment 52. The inlet pressure port 100 extends parallel to the inlet port 58. An outlet pressure port 102 extends from the round body 70 of the outlet segment 54. The outlet pressure port 102 extends parallel to the outlet port 72. In the illustrative embodiment, the inlet pressure port 100 and the outlet pressure port 102 are aligned along an imaginary line 104. The imaginary line 104 extends parallel to the flowpath 90. That is, the inlet pressure port 100 and the outlet pressure port 102 extend parallel to the flowpath 90. The inlet pressure port 100 and the outlet pressure port 102 are configured to couple to a differential pressure sensor (described below).

Figure 7:
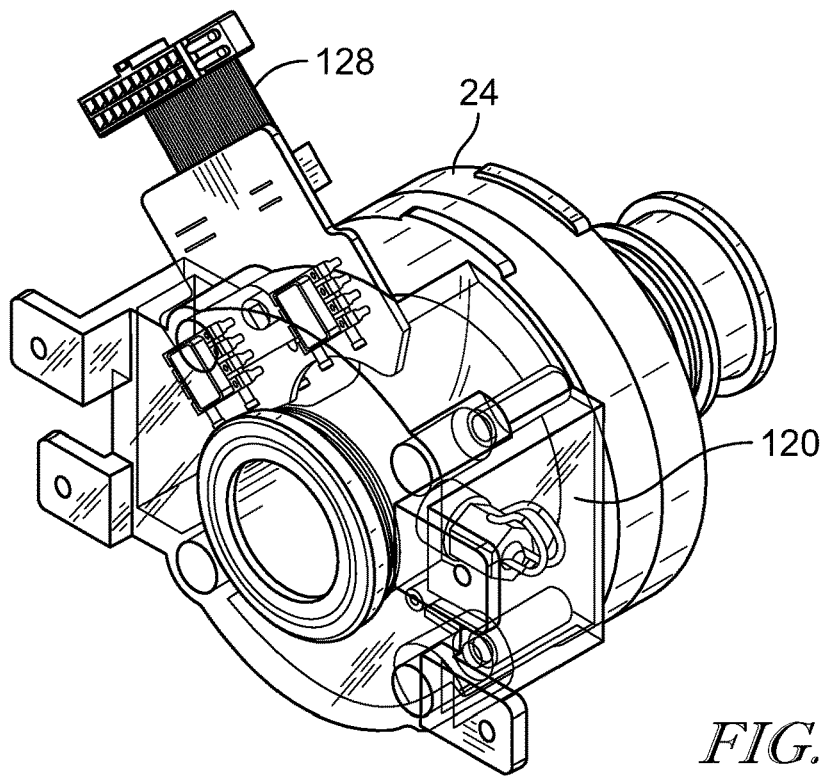
FIG. 7 is a side perspective view of a respiratory module including the flow element shown in FIG. 1.
Figure 8:
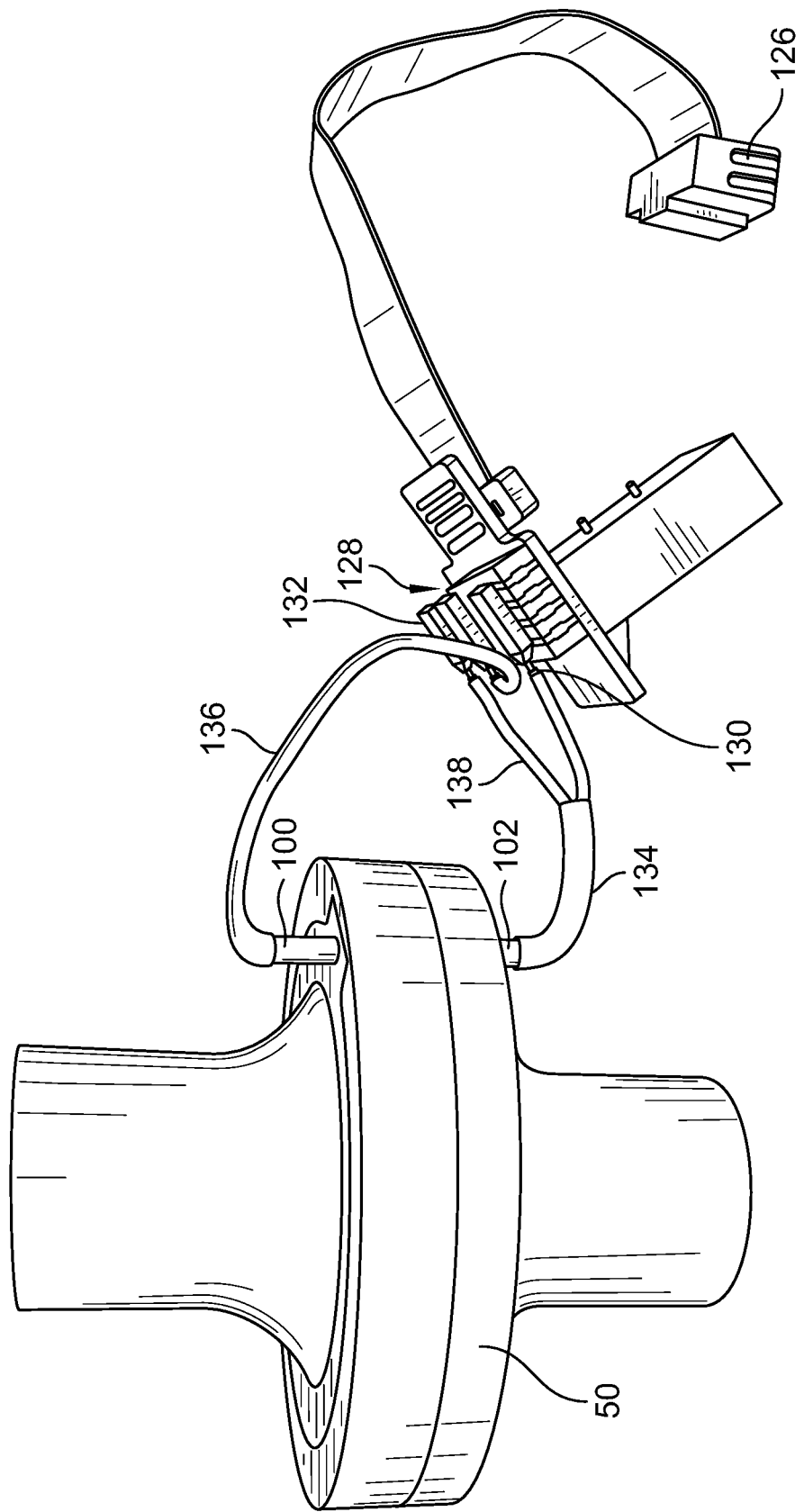
FIG. 8 is an exploded view of the flow element and a pressure transducer.

Referring to FIG. 7, the flow element 24 is positioned within a housing 120 that is configured to be positioned within the respiratory device 10. A printed circuit board 128 is positioned within the housing 120 and includes a pair of differential pressure sensors 130, 132. Referring to FIG. 8 a conduit 134 connects the outlet pressure port 102 to a first differential pressure sensor 130 of the circuit board 128. A conduit 136 connects the inlet pressure port to the first differential pressure sensor 130 and the second differential pressure sensor 132 through a Y-splitter 138. The first differential pressure sensor 130 is configured to output the pressure drop passing through the flow element 24 to derive a flow based on the resistance of the flow element 24. The second differential pressure sensor 132 is configured to output a pressure drop across the patients' airway system. In one embodiment, the first differential pressure sensor 130 is a model number HSCMRRN016MD2A3 differential pressure sensor, and the second differential pressure sensor 132 is a model number HSCMRRN160MDSA3 differential pressure sensor, both available from Honeywell International Inc. of Morris Plains, N.J.

Figure 9:
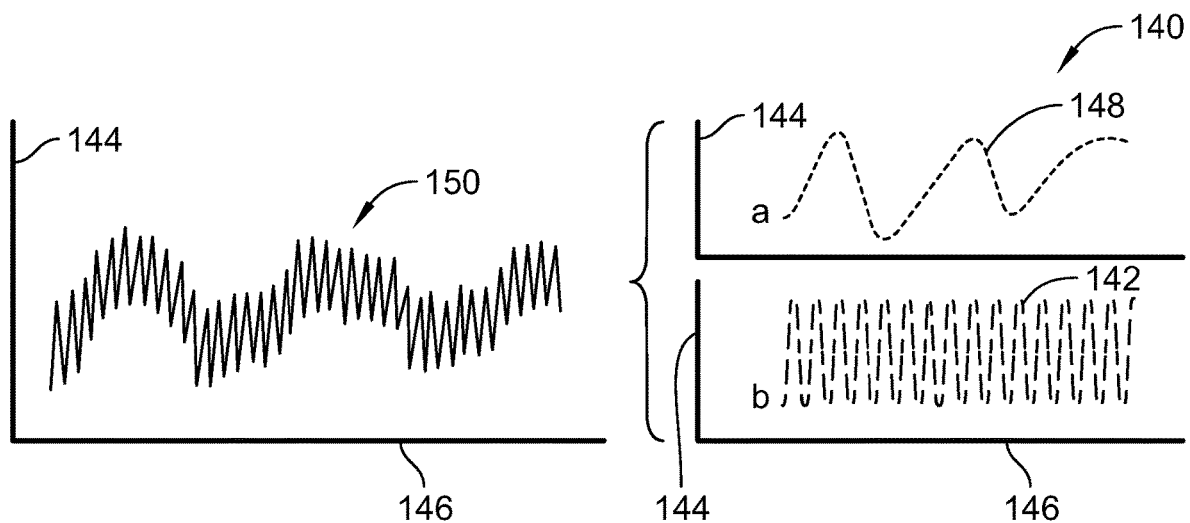
FIG. 9 is a graph of a signal combining a breathing signal of a patient and a pulse having multiple frequencies.
Figure 10:
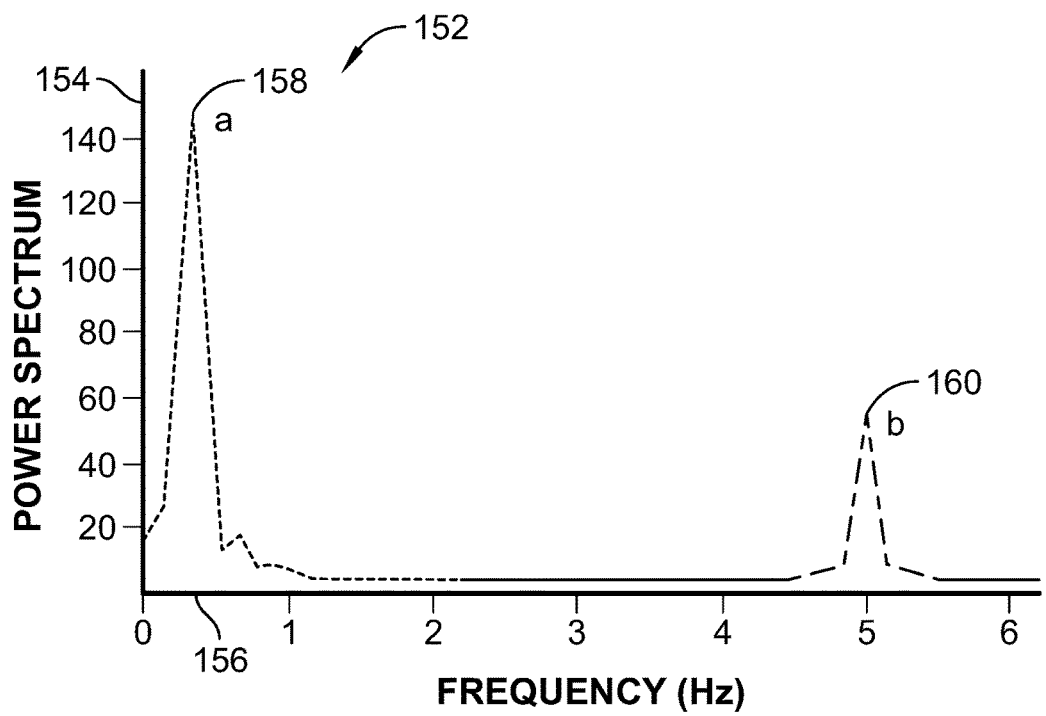
FIG. 10 is a graph of a Fast Fourier Transform of the signal shown in FIG. 9.

Based on the information derived from the differential pressure transducers 132, 130, an efficacy of the therapy administered to the patient from the respiratory device 10 is determined by passing pulses through the flow element 24. Referring to FIG. 9, three graphs are shown including a graph 140 of the patient's breathing waveform 148 in pressure 144 over time 146 and a graph of an external stimulus applied to the flow element 24 in the form of an impulse signal 142 containing multiple frequencies, as shown in the bottom right graph of FIG. 9. By combining the waveform 142 and the impulse signal 148, a combined signal 150 is acquired, as show in the third graph of FIG. 9, which can be used in evaluating a patient's mechanical response to the impulse signal 148. FIG. 10 illustrates the combined signal 150 converted by a Fast Fourier Transform, as shown in the left graph of FIG. 9. The Fast Fourier Transform graph 152 illustrates a power spectrum 154 as a function of frequency 156. As illustrated in FIG. 10, the patient's breathing cycle is represented by a peak 158 having frequency of approximately 0.5 Hz. The impulse signal 148 is represented by a peak 160 having a higher frequency of about 5 Hz.

Based on the graph 152, a respiratory system impedance can be derived which gives the information on the patients' lung resistance and compliance using the below equations:

$$Zrs(\omega) = P(\omega)/V'(\omega) = Rrs + iXrs = Rrs + i(\omega I - 1/\omega C)$$

Zrs(ω) represents an impedance of the patient's breathing cycle, Rrs represents the patient's lung resistance in cmH2Os/L, which is a measure of pressure divided by flowrate, and Xrs represents the patient's lung reactance in cmH2Os/L. Additionally, I represents a patient's lung inertia and C represents the patient's lung compliance. Notably, low frequency oscillations (f<20 Hz) are spread in a lower depth of the airway, and higher frequency oscillations (f>20 Hz) are spread in an upper portion of the airway. Accordingly, the patient's lung resistance and lung reactance before treatment are compared to the patient's lung resistance and lung reactance after therapy using the method shown in FIG. 11.

Figure 11:
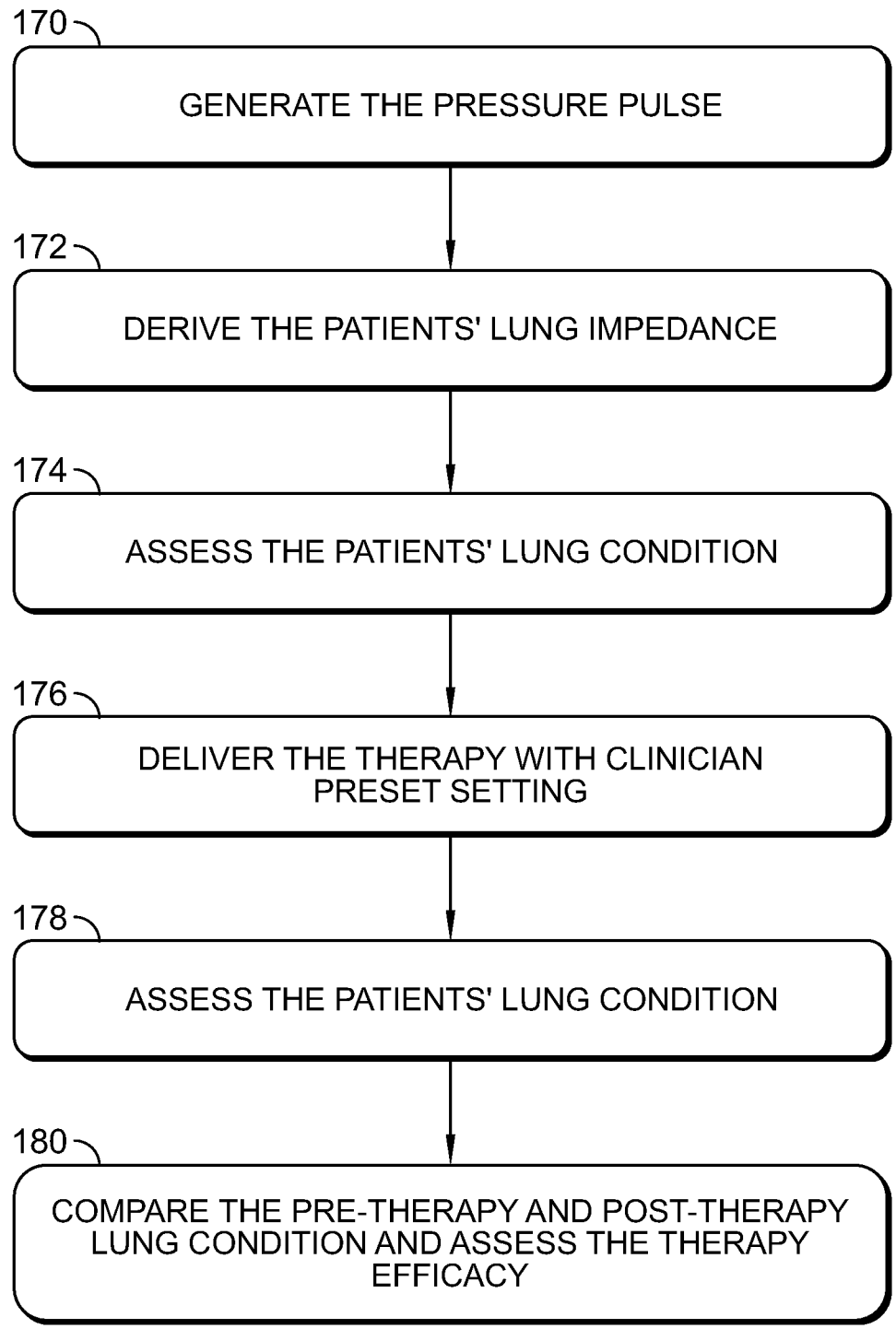
FIG. 11 is a flowchart of a method for determining a therapy efficacy.

At block 170 of FIG. 11, the impulse signal 148 is introduced to the patient's airway. The patient's lung impedance is calculated using the equation set forth above, at block 172. Based on the patient's lung impedance an assessment of the patient's lung condition is evaluated, as indicated at block 174. The therapy is then delivered to the patient, at block 176. After therapy, another impulse signal 148 is introduced into the patient's airway to derive a new patient lung impedance, at block 178. At block 180, the new lung impedance is compared to the lung impedance prior to the therapy to assess the efficacy of the therapy.

For example, FIG. 12 illustrates a lung resistance curve 190 and lung reactance curve 192 at stage 1 of therapy during mucus mobilization when mucus in moved from the lower airway to the upper airway. The lung resistance curve 190 and the lung reactance curve 192 are shown in units of centimeters of water seconds per liter (cmH2Os/L) along the y-axis, and are illustrated over frequency in Hz along the x-axis. In the lung resistance curve 190, the point 200 represents an overall resistance of the respiratory system at a frequency of 5 Hz. The point 202 represents the resistance of the conducting airways at 20 Hz. The line from point 200 to point 202 represents changes in the shape of resistance that are typically associated with heterogeneous obstruction and small airway disease. In the lung reactance curve 192, the point 210 represents overall stiffening (i.e. loss of compliance) of the lungs and obstruction of small airways at a frequency of 5 Hz. The point 212 represents the frequency (10 Hz) at which the reactance is zero, which is indicative of an overall stiffening of the lungs and obstruction of small airways. The area 214 is indicative of overall stiffening of the lungs and obstruction of small airways. Lastly, a change in the point 210 represents the difference between low frequency inspiratory and expiratory resistance.

FIG. 13 illustrates a lung resistance curve 220 and a lung reactance curve 222 at stage 2 of therapy, when mucus is facilitated to cough out of the patient's airway. If the therapy is effective, the following trends should be observed. The resistance at 20 Hz should increase as shown by point 224 indicating an increase in upper airway resistance. Likewise, the resistance at 5 Hz should increase as illustrated by point 226. The line 228 between 5 Hz and 20 Hz should decrease indicating that the lower airway resistance has decreased relative to the initial curve 190. Further, in the lung reactance curve 222, the new curve 230 should shift upward, relative to the initial curve 192, indicating improved lung compliance.

FIG. 14 illustrates a lung resistance curve 240 and a lung reactance curve 242 at stage 3 after the therapy has ended. After therapy, the following trends should occur if the therapy is effective. The resistance at 20 Hz should decrease as represented by point 250. The resistance at 5 Hz should decrease as represent by point 252. Also, the new curve 254 from 5 Hz to 20 Hz should decrease, relative to the curve 220. Each of these decreases is indicative of a decrease in both the upper airway and lower airway resistance. Further, the new reactance curve 260 will shift upward, relative to the curve 230, indicating improved lung compliance.

Figure 15:
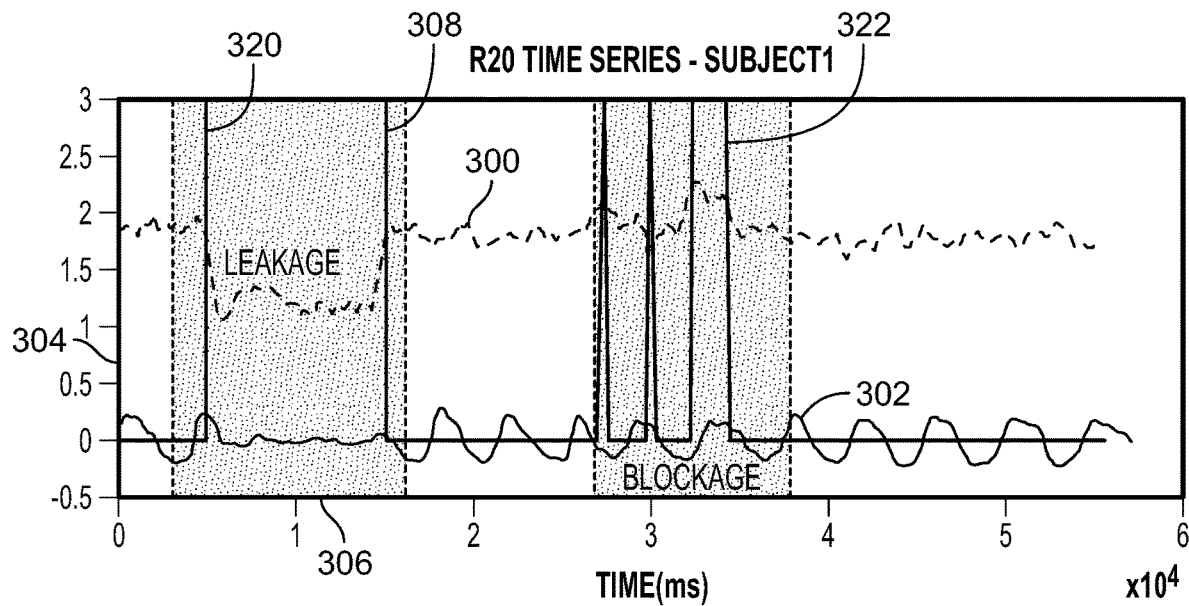
FIG. 15 is a graph of a patient's breathing cycle.
Figure 16:
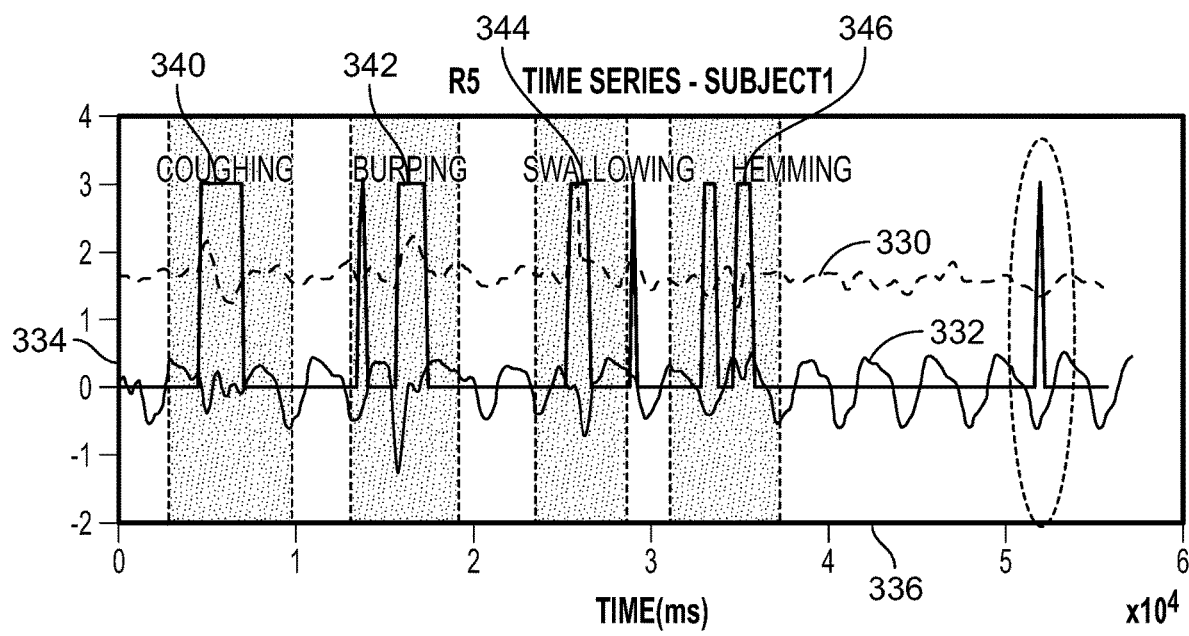
FIG. 16 is another graph of a patient's breathing cycle.

While the above method may be utilized to determine the efficacy of a therapy treatment, there may be several factors that may affect the data. For example, a nose clip, a cheek support, sitting posture of the patient, or motion of the patient may create artifacts in the impedance data. Also, additional tubing, bending in the tubing, or an exhalation port may create artifacts. Artifacts may also be created by glottis closure, coughs, swallowing, or other breathing artifacts. For example, FIG. 15 illustrates a breathing pressure waveform 300 and a resistance curve 302 at 20 Hz as a function of pressure 304 (y-axis) over time 306 (x-axis). Artifacts are indicated by the line 308. As can be seen, an artifact 320 occurs between 0.5 seconds and 1.5 seconds that may be indicative of leakage in the system. Another artifact 322 occurs between 2.5 seconds and 4 seconds that may be indicative of blockage in the system. In another example, FIG. 16 illustrates a breathing pressure waveform 330 and a resistance curve 332 at 5 Hz as a function of pressure 334 (y-axis) over time 336 (x-axis). An artifact 340 is present at 0.5 seconds, which may be indicative of coughing. Another artifact 342 is present between 1 second and 2 seconds, which may be indicative of burping. An artifact 344 is present at 2.5 seconds, which may be indicative of swallowing. Lastly, an artifact 346 is present at 3.5 seconds, which may be indicative of hemming.

Figure 17:
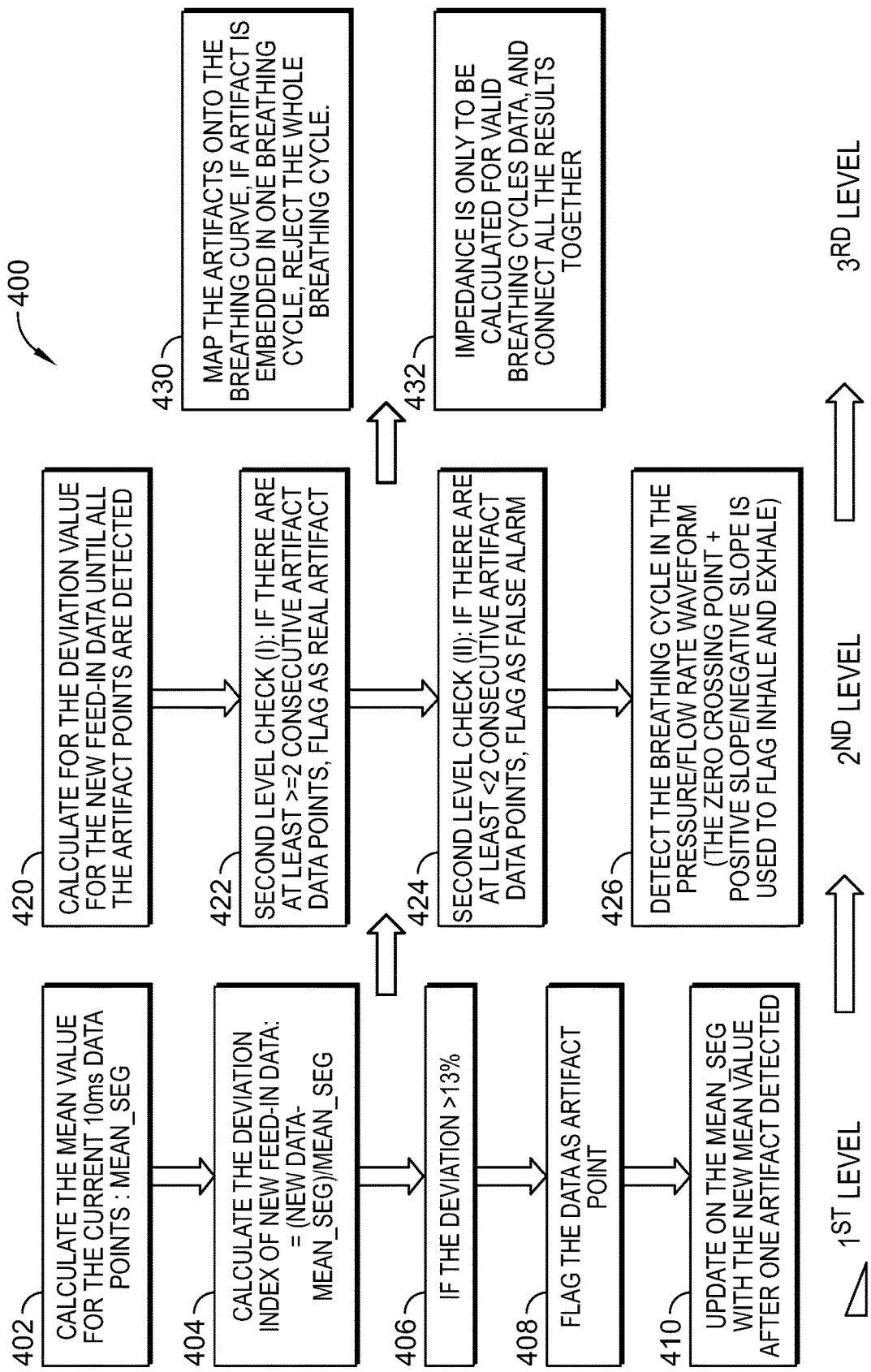
FIG. 17 is a flowchart of a method for removing artifacts from a graph of a patient's breathing cycle.

FIG. 17 illustrates a method 400 for removing artifacts that occurs in three stages. In the first stage, at block 402 a mean value is calculated for 10 milliseconds of data. At block 404, a deviation in the data is calculated by subtracting the original mean value from a newly acquired mean value and dividing by the original mean value to determine a percentage of deviation. It is then determined whether the deviation is greater than 13%, at block 406. It should be noted that other percentages may be utilized to assess the data. At block 408, a deviation greater than 13% is flagged, and the original mean value is updated with the new mean value, at block 410. If at block 406 the deviation is not greater than 13%, the method proceeds to block 420.

In the second stage, at block 420, further deviation values are detected until all of the artifact points are detected. At block 422, the data is assessed to determine whether any consecutive artifact points exist. If so, these points are flagged as real artifacts. At block 424, artifact points that are not consecutive are flagged as false alarms. At block 426, the breathing cycle is detected in the pressure flowrate waveform like those in FIGS. 9-11. Inhaling and exhaling is flagged by adding the zero crossing point to the positive slope to acquire a sum, and dividing the sum by the negative slope.

In the third stage, the artifacts are mapped onto the breathing curve, and if an artifact is embedded in the breathing cycle, the breathing cycle is rejected, at block 430. At block 432, the impedance is calculated only for valid breathing cycles and the results are connected together to determine a curve without artifacts. FIGS. 15 and 16 illustrate resistance and reactance curves, respectfully, both with and without the artifacts.

Figure 18:
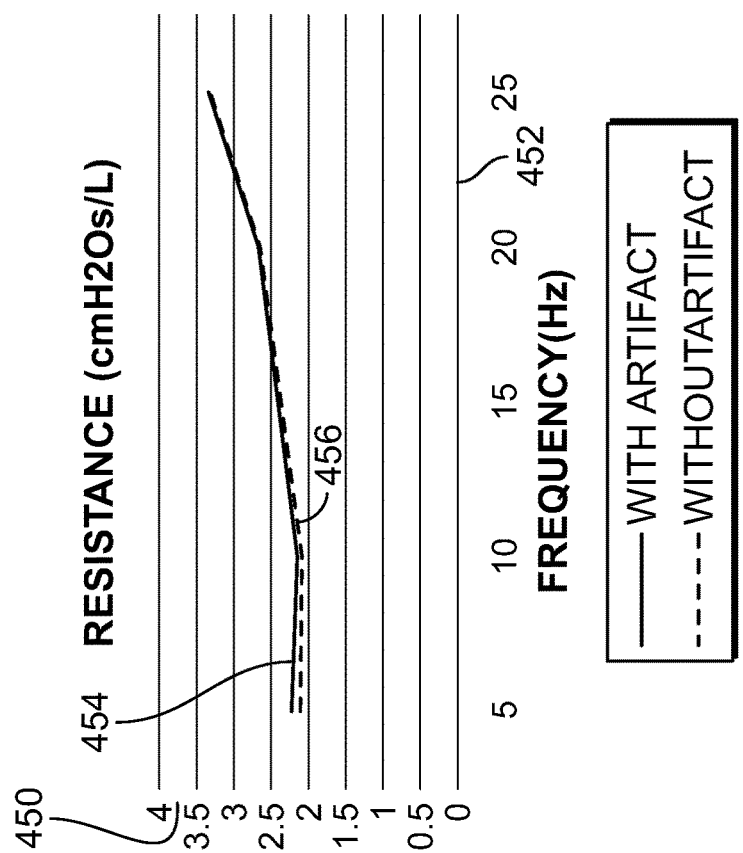
FIG. 18 illustrates a graph of a patient's lung resistance.

Referring to FIG. 18, a patient's lung resistance is illustrated as resistance 450 as a function of frequency 452. A first line 454 illustrates the lung resistance with an artifact. A second line 456 illustrates the lung resistance without the artifact. At 5 Hz, frequency the lung resistance is higher in line 454 than in line 456. Accordingly, by using the method set forth above to remove artifacts, the patient shows lower and improved lung resistance without the artifact, when compared to the lung resistance with the artifact.

Figure 19:
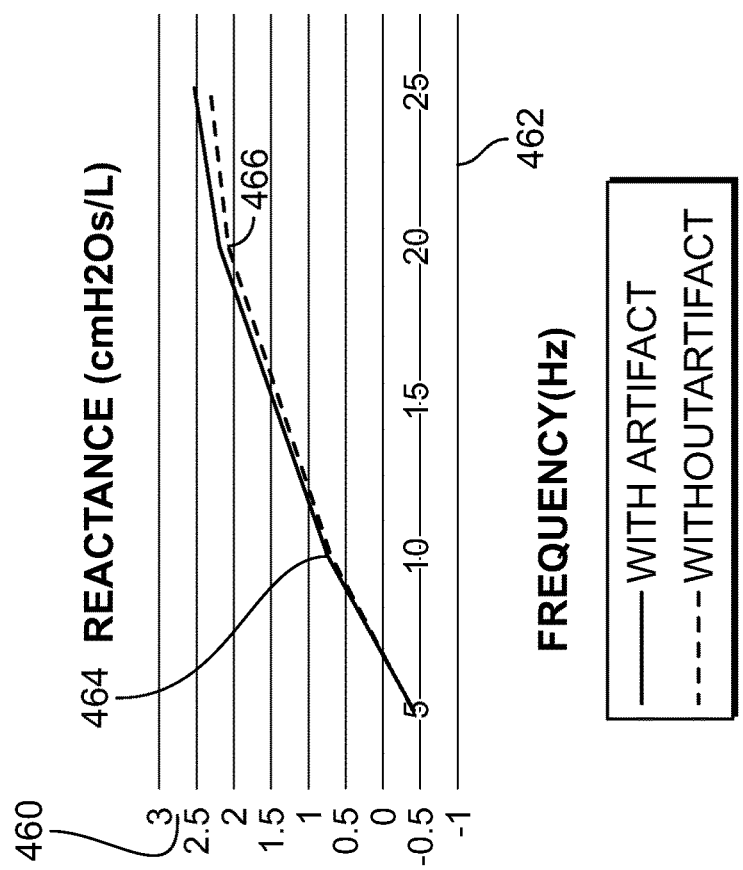
FIG. 19 illustrates a graph of a patient's lung reactance.

Referring to FIG. 19, a patient's lung reactance is illustrated as pressure 460 as a function of frequency 462. A first line 464 illustrates the lung reactance with an artifact. A second line 466 illustrates the lung reactance without the artifact. At 20 Hz. and 25 Hz., the lung reactance is lower and improved without the artifact, when compared to the lung reactance with the artifact. Accordingly, by using the method set forth above to remove artifacts, the patient shows lower and improved lung reactance without the artifact, when compared to the lung reactance with the artifact.

Figure 20:
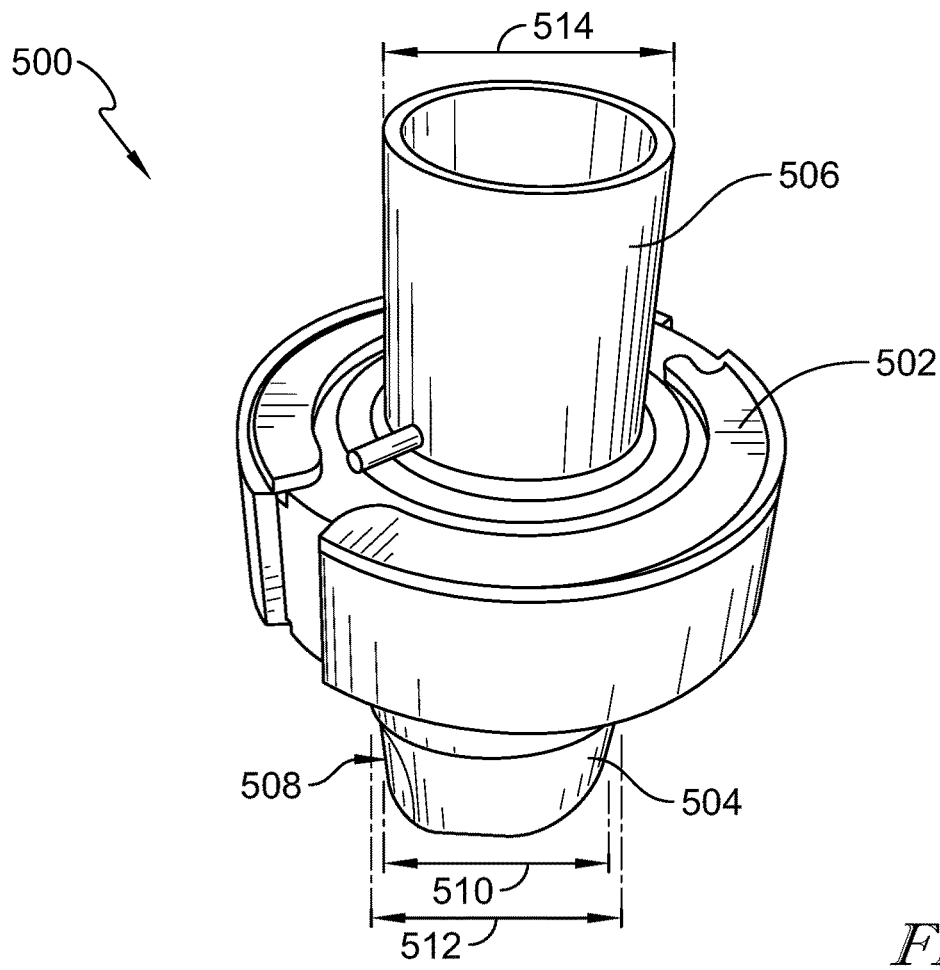
FIG. 20 is a perspective view of another embodiment of a flow element.
Figure 21:
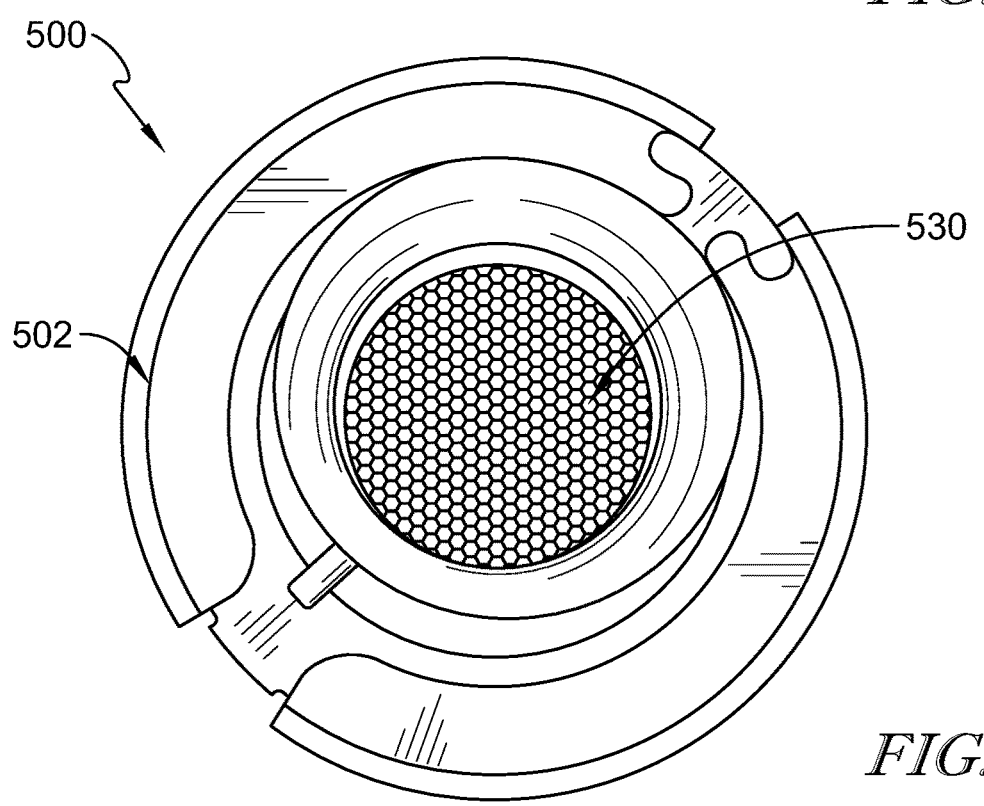
FIG. 21 is a top plan view of the flow element shown in FIG. 20.

FIG. 20 is another embodiment of a flow element 500 having a central body 502 and an inlet 504 and outlet 506 extending from the central body 502. The inlet 504 has an end 508 with a diameter 510 that is less than a diameter 512 of the inlet 504 at the central body 502. The outlet 506 has a diameter 514 that is equal to or greater than the diameter 512. This trumpet shape or dialation of inlet port to a much bigger diameter facilitates achieving laminar flow so that the effective flow area is equivalent to the inlet port size. The central body 502 is sized to retain a filter 530 as illustrated in FIG. 21.

Figure 22:
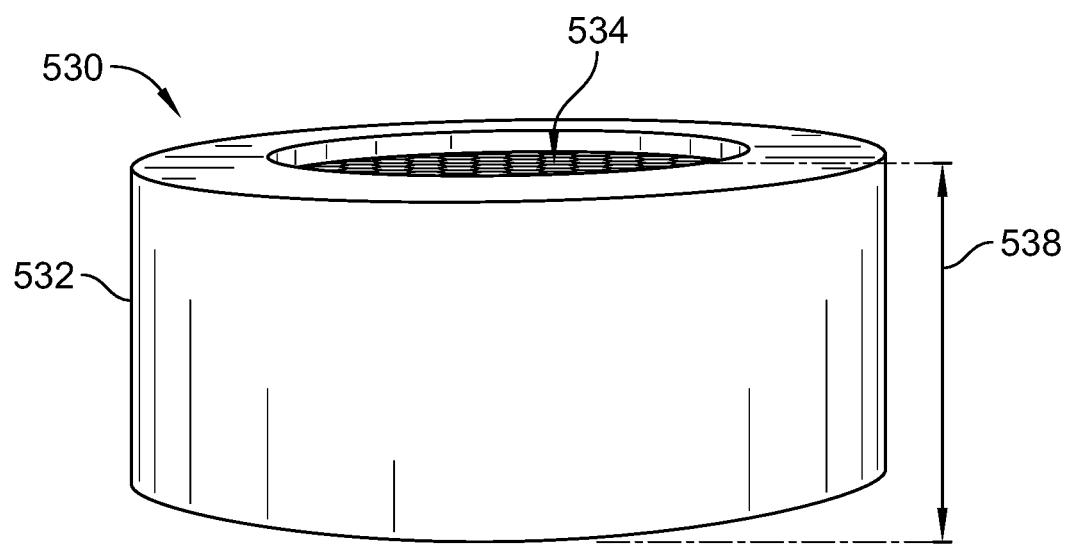
FIG. 22 is a side perspective view of the filter shown in FIG. 21.
Figure 23:
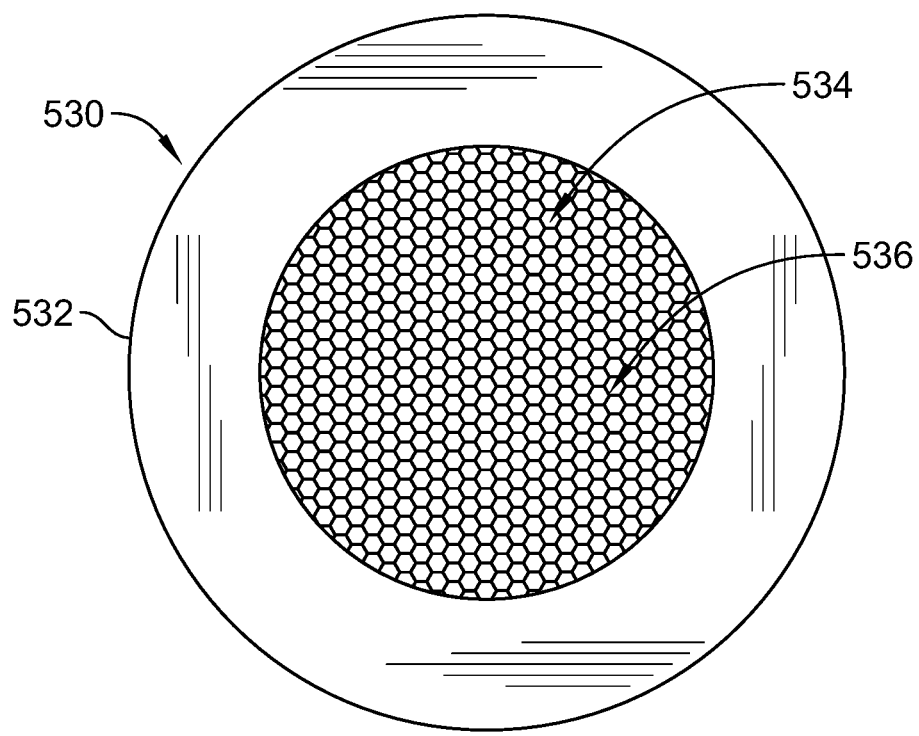
FIG. 23 is a top plan view of the filter shown in FIG. 22.

Referring to FIGS. 22 and 23, the filter 530 includes a gasket 532 that seals a honeycomb 534 within the central body 502. The honeycomb 534 includes a plurality of holes 536 having a diameter of approximately 0.9 mm. The larger diameter reduces the chance of dust and/or moisture becoming stuck in the holes 536 when compared to a mesh or screen design. Accordingly, the user does not have to regularly clean the flow element 500. The honeycomb 534 has a thickness 538 of approximately 1 cm. The thickness facilitates creating a desired pressure drop for sensing flow through the flow element 500.

Although this disclosure refers to multiple embodiments, it will be appreciated that aspects of each embodiment may be utilized with other embodiments described herein.

Although this disclosure refers to specific embodiments, it will be understood by those skilled in the art that various changes in form and detail may be made without departing from the subject matter set forth in the accompanying claims.

The invention claimed is:

1. A method of assessing airway clearance therapy efficacy, the method comprising:
generating a pressure pulse in a respiratory device being used by a patient;
measuring the patient's lung impedance during the pressure pulse, wherein the patient's lung impedance is derived from a Fast Fourier Transform of a combined signal formed by combining a waveform of the patient's breathing with the pressure pulse, wherein the Fast Fourier Transform results in a power spectrum having a patient's breathing cycle represented by a first peak and an impulse signal represented by a second peak;
calculating deviations in data related to the patient's lung impedance to detect deviations in the data that are greater than a predetermined percentage and indicative of artifact points in the data;
assessing whether any consecutive artifact points exist in the data;
mapping the consecutive artifact points onto the waveform of the patient's breathing;
rejecting any breathing cycle in the waveform of the patient's breathing containing the consecutive artifact points;
assessing the patient's lung condition based on the patient's lung impedance;
delivering airway clearance therapy to the patient;
assessing the patient's lung condition after the airway clearance therapy; and
comparing the patient's lung impedance to the patient's lung condition after the airway clearance therapy to determine a therapy efficacy.

2. The method of claim 1, further comprising deriving the patient's lung resistance and lung compliance from the patient's lung impedance.

3. The method of claim 2, further comprising assessing the patient's lung condition based on the patient's lung resistance and lung compliance.

4. The method of claim 2, wherein the patient's lung compliance is a factor of the patient's lung inertia.

5. The method of claim 2, further comprising deriving an overall resistance of a patient's respiratory system based on a graph of the patient's lung resistance.

6. The method of claim 2, further comprising deriving a resistance of a patient's conducting airways based on a graph of the patient's lung resistance.

7. The method of claim 1, further comprising deriving a patient's lung reactance from the patient's lung impedance.

8. The method of claim 7, further comprising determining a compliance of the patient's lung based on the patient's lung reactance.

9. The method of claim 1, wherein comparing the patient's lung impedance to the patient's lung condition after the airway clearance therapy to determine a therapy efficacy further comprises comparing the patient's lung impedance before the airway clearance therapy to the patient's lung impedance after the airway clearance therapy.

10. The method of claim 1, further comprising mapping a breathing waveform onto a real time impedance curve to identify intact breathing cycles.

11. The method of claim 10, further comprising connecting the intact breathing cycles to calculate the patient's lung impedance.

12. The method of claim 1, further comprising deriving the patient's lung resistance from the patient's lung impedance.

13. The method of claim 12, further comprising deriving an overall resistance of a patient's respiratory system based on a graph of the patient's lung resistance.

14. The method of claim 12, further comprising deriving a resistance of a patient's conducting airways based on a graph of the patient's lung resistance.

15. The method of claim 1, further comprising deriving the patient's lung compliance from the patient's lung impedance.

16. The method of claim 15, further comprising deriving the patient's lung compliance as a factor of the patient's lung inertia.

17. The method of claim 1, further comprising:
detecting a breathing signal;
updating a baseline of the breathing signal to a new baseline based on a deviation in the baseline of the breathing signal.

* * * * *